(12) United States Patent
Irion et al.

(10) Patent No.: US 6,190,308 B1
(45) Date of Patent: *Feb. 20, 2001

(54) ENDOSCOPIC VIDEO SYSTEM FOR CORRECTING A VIDEO IMAGE OF AN OBJECT TO BE STUDIED

(75) Inventors: Klaus Irion, Liptingen (DE); Karl-Heinz Strobl, Fiskdale, MA (US); Uwe Faust, Stuttgart (DE); David Chatenever, Santa Barbara, CA (US)

(73) Assignee: Karl Storz GmbH & Co., KG (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/011,939
(22) PCT Filed: Aug. 19, 1996
(86) PCT No.: PCT/DE96/01540
§ 371 Date: May 26, 1998
§ 102(e) Date: May 26, 1998
(87) PCT Pub. No.: WO97/07627
PCT Pub. Date: Feb. 27, 1997

(30) Foreign Application Priority Data

Aug. 17, 1995 (DE) ............................................. 195 30 401
Aug. 18, 1995 (DE) ............................................. 195 30 453

(51) Int. Cl.[7] ........................................................ A61B 1/04
(52) U.S. Cl. ............................ 600/109; 600/921; 348/65; 348/188
(58) Field of Search .................................... 600/101, 109, 600/118, 127, 921; 348/65, 71, 76, 73, 175, 188, 187, 176; 359/110

(56) References Cited

U.S. PATENT DOCUMENTS

| | | | |
|---|---|---|---|
| 4,370,641 | * 1/1983 | Kantor et al. | 348/175 |
| 4,513,319 | * 4/1985 | Breimer et al. | 348/176 |
| 4,544,952 | * 10/1985 | Pham van Cang | 348/188 |
| 4,608,593 | * 8/1986 | Miyaji et al. | 348/188 |
| 4,658,286 | * 4/1987 | Schwartz et al. | 348/175 |
| 4,991,007 | * 2/1991 | Corley | 348/188 |
| 5,179,437 | * 1/1993 | Kawada et al. | 348/188 |
| 5,222,477 | * 6/1993 | Lia | 600/166 |
| 5,387,932 | * 2/1995 | Morioka | 348/65 |

* cited by examiner

Primary Examiner—John P. Leubecker
(74) Attorney, Agent, or Firm—St. Onge Stewart Johnston & Reens LLC

(57) ABSTRACT

An endoscopic video system for correcting a video image of an object to be studied has a processing unit controlling an electronic image recorder which has a multiplicity of image elements, each generating an output signal upon illuminating a known test object. The processing unit has a learning mode of operation, wherein it determines and records a correction value corresponding to a difference between an output signal of the known test object and a generated one by each of the image elements, and a recording mode, wherein an output signal generated by each image element upon illuminating an object to be studied is adjusted at the correction value.

27 Claims, 1 Drawing Sheet

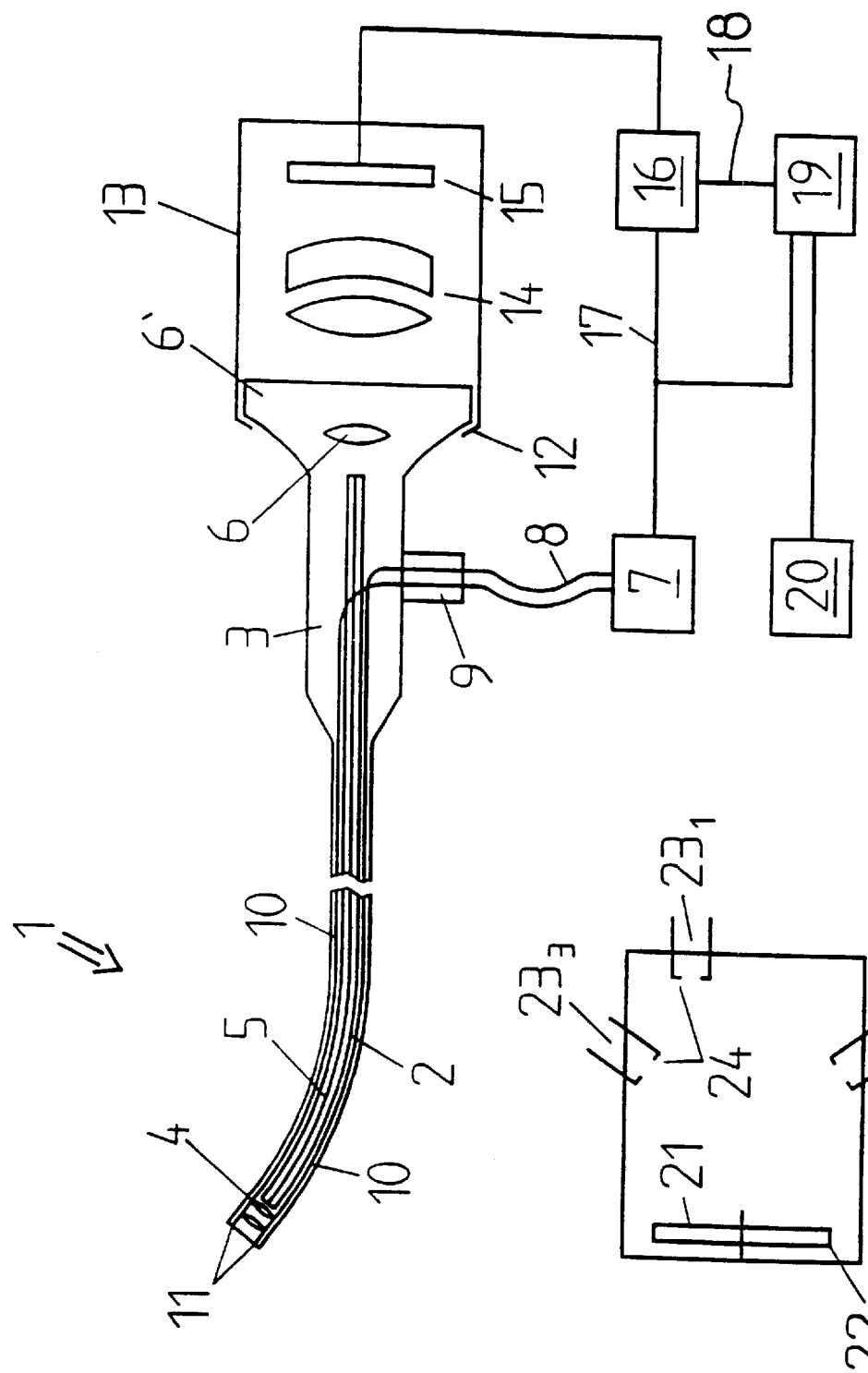

ENDOSCOPIC VIDEO SYSTEM FOR CORRECTING A VIDEO IMAGE OF AN OBJECT TO BE STUDIED

FIELD OF THE INVENTION

The present invention relates to an endoscopic video system for correct a video image of an object to be studied, as well as to a process for calibrating such a video system. Endoscopic video systems of this type are employed for various applications in the technical as well as in the medical field.

BACKGROUND OF THE INVENTION

Endoscopic video systems are known, by way of illustration, from DE-A-32 04 316. The endoscopic video system described in this printed publication is provided with an illumination fiber bundle and an imaging fiber bundle. The illumination fiber bundle guides the light of an illumination device to a light exit aperture at the distal end of the endoscope. An endoscope lens disposed at the distal end of the endoscope images the object field illuminated by the illumination device. This image of the object field is transmitted by the imaging fiber bundle to an electronic image recorder which is disposed proximally and can be, by way of illustration, a vidicon tube or a charge-coupled device such as a CCD chip.

Hitherto fiber bundles which are "ordered" and respectively "coherent" have been employed as imaging fiber bundles in endoscopes. What is meant thereby is that the light entry surface and the light exit surface of each optical fiber of the fiber bundle is located, always in relation to the same position, on the lens plane (i.e., image plane of the endoscope lens) and the image plane (i.e., lens plane of the image recorder).

However, the production of ordered fiber bundles is complicated and therefore expensive. In particular, waste is quite high because, on the one hand the individual fibers break or are otherwise damaged during production, and on the other hand sorting the individual fibers is not always optimal.

In the endoscopic video system known from DE-A-32 04 316, the imaging fiber bundle is an incoherent bundle. What is meant thereby is that the entry-side end and the exit-side end of each fiber are not disposed at the same relative position in the image plane of the endoscope lens and in the lens plane of the image recorder so that the transmitted image in the lens plane of the image recorder is "mixed up". With regard to this, reference is made to page 7, lines 7 to 14 of DE-A-32 04 316.

A decoder, or an image processing unit, corrects the "incoherent" image signal from the image recorder in such a manner that the image is "coherently" represented, by way of illustration, on a monitor.

In the generic endoscopic video system known from DE-A-32 04 316, the relative orientation of the lens-side ends of the incoherent fiber bundles with respect to the image-side ends prior to inserting the fiber bundle into the endoscope is fixed permanently, or "once and for all". (cf. page 8, lines 26f of DE-A-32 04 316).

BRIEF SUMMARY OF THE INVENTION

The present invention is based on an understanding that a video system is needed which permits not only correction of possible incoherencies of the imaging fiber bundles, but also a wide elimination of other typical imaging errors of generic endoscopic video systems. The present invention is based in particular on an understanding that a substantial source of image falsifications, or variances, is the illumination of the object field by the illumination device and the downstream illumination fiber bundle.

Thus, it is an object of the present invention is to improve a generic endoscopic video system in such a manner that other typical image falsifications, or typical variances, of the endoscope are eliminated.

An element of the present invention is that detection and storage of the necessary corrections of the image of the video system does not occur prior to assembling the endoscope, but rather during operation of the endoscope video system using all the components required therefore, and preferably using the illumination device which is to be subsequently employed for recording the endoscope images.

Therefore, an image processing unit is provided with a "learning mode" and a "recording mode". In the learning mode, the image of at least one known test object is recorded, which preferably is illuminated by the illumination unit. The image processing unit compares, in the learning mode, the output signal of each element of the image from the image recorder with a predetermined desired output signal from the test object. The image processing unit determines therefrom, for each image element, the change in intensity and color of the recorded image relative to that of the test object resulting from the variances in illumination due to the lens edge cut-off, transmission errors of the image transmitter, and variances in the sensitivity of the image recorder, and determines therefrom a correction value assigned to the respective image element. In the recording mode, the image processing unit corrects the respective output signal from each image element by means of the correction value assigned to that image element.

Therefore, the invented endoscopic video system permits the correction of errors of the entire system and not only of single components of the system, such as by way of illustration, is the case in the system known from DE-A-32 04 316, which corrects only disorder in the imaging fiber bundle.

A special advantage of the invented endoscopic video system is that the brightness of the image can be evened over the entire object field in use conditions. Nearly all endoscopic images have a center-emphasizing basic brightness distribution which usually diminishes with the radius and which can, furthermore, be inhomogenous. This has a number of possible causes, some of which are as follows:

(1) Due to the focusing of the lamp helix, the non-uniform arrangement and design of the optical fibers in the optical cable between the illumination device and the endoscope, the non-uniform arrangement and design of the optical fibers in the endoscope, and the arrangement of distal light exit apertures, the object field of the endoscope lens is illuminated with a radial distribution of light which is superimposed by random variances. Although a variety of patent applications describe that a more homogeneous distribution of light can be obtained by means of an improved distal-side optical fiber arrangement, and that illumination can be made more homogeneous thereby, uniform illumination using these arrangements is unachievable.

(2) Most endoscope lenses have an "edge cut-off" in the transmission function which usually is larger than the radial decrease of the transmission function which is inversely proportional to the fourth power of the distance from the optical axis (i.e., the "$r^4$ cut-off").

(3) The image transmission system also has an edge cut-off if relay lens systems or gradient lenses are employed. If imaging fiber bundles are used, the result is additional variances caused by broken fibers, or fibers with reduced overall transmission or different spectral transmission compared to most of the fibers.

(4) The individual image elements of the image recorder may have different sensitivity.

According to the present invention the following is undertaken to correct the non-uniform basic image brightness as well as other imaging errors.

In the learning mode, one test object or a multiplicity of test objects are placed in succession in the object field of the endoscope. These test objects may be a matt (e.g., white) glass which is illuminated from the rear, a homogeneous gray or white chart, homogeneous color charts, preferably with pure prime colors, and/or charts which permit detection of distortion of the whole system comprising a lens, an image transmitter and an image recorder. These charts are disposed in such a manner that they stand perpendicular to the viewing direction of the endoscope and are spaced in a certain manner.

In order to meet these conditions, a test cavity is preferably provided into which, in the learning mode, the distal end of the endoscope is inserted and in which the test object(s) (i.e. test charts) are disposed such that they are in the object field of the endoscope lens.

If the image errors of the "whole system" are to be corrected, the respective test chart disposed in the object field of the lens is illuminated by the light leaving the light exit aperture(s) at the distal end of the endoscope, while preferably using the illumination device and the optical cable which also are subsequently going to be utilized for recording the endoscope images.

On the other hand, if the image errors of only the "imaging system" are to be corrected, a matt glass which is homogeneously illuminated from the rear is preferably employed as the test chart.

The image processing unit calculates a two-dimensional filter matrix from the image of each test chart; for imaging a homogeneous gray or white chart, the filter matrix is basically inverse to the "endoscope white image". Preferred is if, in order to minimize the noise caused by the recording electronics, a number of "endoscope white images" are detected and averaged for determining the inverse filter matrix.

In order to correct certain image errors various different single measures adapted to the respective image error can be conducted by the image processing unit.

For example, the image processing unit compensates for the distribution of brightness diminishing in the radial direction toward the edge of the endoscope by means of image standardization carried out over all the image elements, thereby yielding a largely uniformly bright image.

Furthermore, the image processing unit can amplify the signals from the image elements, which are applied by fibers with relatively high transmission losses, in such a manner that the brightness of these image elements correspond to the brightness of the adjacent image elements.

In order to compensate for "dark spots" in the illumination, the image processing unit can amplify the signals from the individual image elements or from groups of image elements in such a manner that variances in the illumination of the object field are compensated.

In addition, the image processing unit can modify the color information of the signals from the image element, which are applied by fibers with spectral transmission properties which differ from most of the fiber bundle, by conversion of the color scale in such a manner that the color information of the image element corresponds to that of the adjacent image elements. The color compensation can be conducted by the transformation RGB (red, green, blue) in HIS, with H standing for the color value, S for color saturation and I for intensity. In this manner, by way of illustration, the occasionally occurring "yellow tinge" of fibers can be compensated.

The invented concept, that the image processing unit "learns" in the learning mode to correct the endoscope image by electronically influencing individual image elements in such a manner that the transmission errors caused by the faulty transmission properties of the whole system and, in particular of the fiber bundle, can no longer be visibly seen, permits not only correction or compensation of differences in brightness, but also other image errors. The image processing unit not only modifies the output signals from the individual image elements but also partially "resorts" the image elements.

The use of a test chart on which there is, by way of illustration, a grid permits determination of the distortion of the whole system. The image processing unit can then compensate for the distortion of the whole system by means of a partial image shift or image transformation, carried out over all the image elements.

The effect of aging in the imaging optical bundle causes, in particular in flexible endoscopes, the breakage of, and therefore the failure of, individual fiber elements. Basically only a very small part of the image information is lost thereby. Due to the very high contrasts between the image transmitting fibers and the defective fibers (which appear as black dots), such image failures, however, are subjectively very disturbing.

In one embodiment, the image processing unit replaces the signals from the image elements which are applied by defective fibers with image information of adjacent image elements which are not applied by defective fibers. However, prior to this, the electronic image information of the defective fiber elements has to be localized. This can also be achieved by imaging a homogeneous test object. Therefore, subjectively disturbing image errors occurring during the lifetime of a video endoscope can be eliminated by simply switching to the learning mode and recording the image of a test chart.

The same applies to the signals from image elements which are "applied" from the spaces between the fibers. The image processing unit replaces the signals from these image elements with the image information of adjacent image elements applied by light transmitting fibers.

Usually endoscope lenses are not provided with an adjustable aperture. Exposure control or regulation, therefore, occurs by setting the lamp power of the illumination device and/or by changing the shutter speed of the image recorder. In particular, the image recorder control unit sets the different shutter speeds of the imaging recorder electronically by varying the "photon integration time" over the individual image elements.

If the impinging lamp power is changed, the spectrum of the light emitted by the lamp also partly changes. Aging can also alter the spectrum of the light emitted by a lamp and, in particular, by a gas discharging lamp. The image processing unit can compensate for the color changes of the image resulting from fluctuations of the color temperature of the lamp(s) of the illumination device causing the different impinging power and/or aging of the lamp(s).

In one embodiment of the invention, the image processing unit calculates, in the learning mode, a correction function by which, in the recording mode, the disturbing grid lines, which are generated by light-impermeable cladding of the individual fibers of the fiber bundle, are made invisible. These grid lines represent a periodic two-dimensional pattern in the local area which is compensated by a sine function, which is employed as the correction function in the frequency range.

Of course, in the invented endoscopic video system, just as in the state of the art, an imaging fiber bundle can be used which is at least partly a disordered bundle. The image processing unit alters the arrangement of the individual image elements electronically in such a manner that the reproduced image corresponds to the fiber-bundle-entry side image.

The allocation of the individual image elements of the image recorder with respect to the original image positions (i.e. the actual/desired allocation) occurs in the learning process in that an image of the test chart is recorded which permits an unequivocal allocation of the desired positions of each image element and that the image processing unit determines the allocation of the actual positions with respect to the desired positions. The image processing unit compiles the allocation using the test image and stores the allocation, by way of illustration, in the form of a table.

In view of the fact that, with flexible endoscopes, various image errors, such as by way of illustration the nonuniformity of illumination, the transmission of the imaging fiber bundle or the distortion of the image, can vary due to bending of the endoscope, the image processing unit determines correction values corresponding to the bending of the endoscope.

Furthermore, the image processing unit provided in the invented endoscopic video system can generate an electronic image field shutter which is smaller than the endoscope image field shutter so that the disturbing cut-off at the immediate edge of the image is no longer visible. Moreover, the image processing unit can subject the image to other manipulations, such as by way of illustration an electronic image erection, electronic reflection (reverse video), etc.

The present invention can be utilized in a variety of different types of endoscopes. Thus, the image recorder can be disposed distally, such as by way of illustration in a kind of probe, and the image of the endoscope lens can be recorded directly or via an optical adaptation system, which, however, does not serve as the image transmitter. Of course, the image recorder can also be disposed proximally. The image recorder may be built "permanently" into the endoscope or, as is known, into a video camera which is flanged to the eyepiece of the endoscope. Particularly in this event, the embodiment of the invention which permits calibration during each examination is especially advantageous. The image transmitter, which transmits the image generated by the endoscope lens to the proximal end of the endoscope, and which is required if the image recorder is disposed proximally, may be a relay lens system which, in particular, is composed of rod lens systems and/or of elements having a non-uniform refraction index, or may take the form of an imaging fiber bundle, such as employed in flexible or thin bore rigid endoscopes.

A variety of different recorders, including recording tubes, may be used as an image recorder. Especially preferred, however, is if the image recorder is provided with at least one CCD chip, because, in a sensor of this type, the number of sensor elements is greater than the number of fibers of the fiber bundle.

BRIEF DESCRIPTION OF THE DRAWINGS

The present invention is made more apparent in the following drawings wherein a preferred embodiment is shown and wherein:

FIG. 1 is a schematic depiction of a preferred embodiment of the present invention, and FIG. 2 is a schematic depiction of the test cavity and test charts employed in this preferred embodiment.

DETAILED DESCRIPTION OF A PREFERRED EMBODIMENT

FIG. 1 shows an endoscope 1 comprising a flexible insertion part 2 and a proximal part 3. The insertion part 2 can be steered or can be tangentially bent in a known manner by means of pulls, operating elements, etc. (not depicted). Disposed at the distal end of the insertion part 2 is an endoscope lens 4 which, without the intention of limiting the general applicability of the present invention, in the depicted preferred embodiment is a "front viewing lens" (i.e. the optical axis of the lens coincides with the longitudinal axis of the insertion part 2). Of course, within the scope of the present invention, lenses whose optical axis includes an angle with the longitudinal axis of the insertion part 2 can also be utilized. An imaging fiber bundle 5 transmits the image of lens 4 to the proximal end in such a manner that it can be observed with an eyepiece 6, which is disposed in the proximal part 3.

For illumination of the object field of the endoscope lens 4, an illumination device 7 with lamp (not depicted) is provided. An optical cable 8 conveys the light of this lamp to a light connection 9 which is attached to the proximal part 3. The light connection 9 is connected via illumination bundle 10 to light exit apertures 11 at the distal end of the endoscope. The light leaving light exit apertures 11 illuminates the object field of the endoscope lens 4.

In the shown preferred embodiment, a video camera 13, which is provided with a video lens 14 and, if need be, without limiting the overall applicability of the present invention, with a CCD chip as the image recorder, is attached to the eyepiece flange 6' by means of a known flange 12. Of course, other image recorders or a multiplicity of chips can be utilized for the different primary colors.

Video camera 13 is controlled by a control device 16, which also generates a conventional video output signal, such as by way of illustration a RGB signal. The control device 16 is connected via a control line 17 to the illumination device 7 and provides light regulation controls to regulate the light output provided by the illumination device 7.

The arrangement described in the preceding is known. Corresponding endoscopes and video units are produced in series and sold, by way of illustration, by Karl Storz GmbH & Co., the assignee of this application.

The video signal output connection of the control device 16 is connected via a line 18 to the input connection of an image processing unit 19, which corrects, further processes, and, in particular, represents the video output signal on a monitor 20 in real time.

Corresponding image processing units are also known and can, by way of illustration, be provided with a personal computer ("PC") of industrial standard or with a special image processor. The assignee of the present invention also provides under the brand "TwinVideo" a suitable image processing unit which carries out image rotations and reflections.

In addition, the signal applied to the control line 17 also is applied to the image processing unit 19.

In the following, the invented manner of operation of the image processing unit 19 is described.

The image processing unit 19 permits real time image processing with a priori knowledge of image errors. In off-line processing, the to-be-corrected image transmission properties are electronically detected and inverse image operations are calculated and stored.

Thus, the image processing unit 19 is provided with a "learning mode" and a "recording mode".

In the learning mode the image of at least one known test object, which is preferably illuminated by the illumination device, is recorded. The image processing unit 19 compares the output signal of each image element of the image recorder 15 with a predetermined desired output signal for this test object, and determines therefrom for each image element the change in intensity and color of the recorded image compared to the test object. Such change may be caused by variances in illumination, by lens edge cut-off, by transmission errors of the image transmitter, and/or by variances in the sensitivity of the image recorder. The image processing unit 19 uses this information to determine a correction value assigned to each respective image element.

In the recording mode the image processing unit 19 corrects the respective output signal of each image element by means of the correction value assigned to that image element.

In addition to real time image processing with a priori knowledge of image errors, real time image processing with adaptive error correction is also possible. Preferably, such real time image processing with adaptive error correction can also be superimposed on the real time image processing with a priori knowledge of image errors.

In particular, image processing may proceed, by way of illustration, as follows.

In order to compensate for diminishing brightness of the whole imaging system, the endoscope image of a white, homogeneous matt glass, which is illuminated from the rear without endoscope illumination, is recorded.

Similarly, in order to correct for inhomogeneous basic image brightness caused by the endoscope-specific illumination and the optical transmission properties of the endoscope, the image of a homogeneous, white surface which stands perpendicular to the viewing direction of the endoscope is recorded.

In both cases, a two-dimensional filter matrix is calculated, which is inverse to the "endoscope white image". In order to minimize noise effects caused by the recording electronics 16, a multiplicity of endoscope white images are averaged.

In order to substitute image points when there are fiber defects, such as occur due to aging of the image optical fibers, image processing may proceed as follows.

Detection of strays due to broken fibers of bundle 5 follows homogenizing the basic brightness of the image. All black pixels are detected via an intensity threshold value criteria. All pixels lying in intensity below a certain threshold value are replaced by the "average maximum" of the active pixel within a certain search area. This process also permits recording spaces between fibers which impinge upon the individual image elements or pixels.

The arithmetic operations carried out in the image processing unit 19 are known and are therefore not explained in more detail here.

The preceding description shows that conducting the so-called learning mode is essential for correcting the image errors.

In the learning mode, particularly if a distortion correction is carried out, the test chart has to be disposed at a certain distance from the distal end surface of the endoscope lens and at a right angle to the lens axis.

For this reason, according to the present invention a test cavity is employed (FIG. 2), in which a number of test charts 21 are disposed, by way of illustration, on a disk 22 in such a manner that they can be inserted in succession into the object field of lens 4 of endoscope 1. Endoscope 1, which is a front viewing type, is inserted for this purpose into an aperture $23_1$ assigned to this type of endoscope. Correspondingly, there are apertures $23_2$ for lateral viewing and $23_3$ for retro-endoscopes, ensuring that the viewing direction of the endoscope is disposed exactly perpendicular to the respective test chart. Thus, the test cavity permits conducting the learning mode for endoscopes with different viewing directions. Stops 24 in the apertures ensure that the predetermined distance is maintained exactly.

In the preceding the present invention is described using a preferred embodiment without the intention of limiting the scope or spirit or the overall inventive concept indicated in the specification and the claims.

What is claimed is:

1. An endoscopic video system having
   an endoscope,
   an illumination device,
   an optical fiber guide for transmitting light from said illumination device to at least one light exit aperture at a distal end of said endoscope,
   an endoscope lens, which images an object field illuminated by said illumination device and which is disposed at the distal end of said endoscope,
   an electronic image recorder having a multiplicity of image elements, which records an image of said lens to produce an image signal, and
   an image processing unit which processes and depicts the image signal from said image recorder in real time on a display unit, characterized by the following features:
   said image processing unit is provided with a learning mode and a recording mode,
   at least one known test object illuminated by said illumination device to have an image of the one known test object recorded in said learning mode,
   said image processing unit compares in said learning mode the output signal from each image element of said image recorder with a predetermined desired output signal for said one known test object, determines therefrom for each said image element the deviation in intensity and color of the recorded image compared to said test object, resulting due to one of a group of factors including: variances in the illumination, lens edge cut-offs, variances in sensitivity of said image recorder, and combinations of these, and determines therefrom a correction value assigned to the respective image element, said correction value being formed from one of a group of output signals including from each said image element, from the adjacent image elements, from a plurality of image elements, and combinations of these, wherein the determination of the correction value for each respective image element is independent of the determination of the correction values for all other image elements,
   and an object to be studied illuminated by said illumination device in said recording mode, said image processing unit corrects the respective output signal from each image element representing said object to be studied by means of the correction value assigned to said image element in said learning mode.

2. A video system according to claim 1, including an image transmitter which transmits the image generated by said endoscope lens to a proximal end of said endoscope.

3. A video system according to claim 2 characterized by the fact that said image transmitter is provided with at least one relay lens system comprising a rod lens system.

4. A video system according to claim 2, characterized by the fact that said image transmitter is provided with an imaging fiber bundle.

5. A video system according to claim 4, charactrized by the fact that said image processing unit calculates in the learning mode a correction function via which the disturbing grid lines, which are generated by the light-impermeable fiber cladding of the individual fibers of the fiber bundles, occurring in the image are made invisible in said recording mode.

6. A video system according to claim 5, characterized by the fact that said grid lines represent a periodical 2-dimensional pattern in a local area which is compensated via a sine function as the correction function in the frequency range.

7. A video system according to claim 4, characterized by the fact that said endoscope is a flexible endoscope and that said image processing unit determines the correction values in correspondence to bending said endoscope.

8. A video system according to claim 2, characterized by the fact that said image transmitter is provided with at least one relay lens system comprising elements having a non-uniform refraction index.

9. A video system according to claim 1, characterized by the fact that said image recorder is provided with at least one CCD chip.

10. A video system according to claim 1, characterized by the fact that said one known test object is selected from a group comprising: a homogeneous gray chart, homogeneous color charts, charts which permit detection of distortion of the lens, the image transmitter and the image recorder, and combinations of these.

11. A video system according to claim 1, characterized by the fact that a test cavity is provided into which in said learning mode a distal end of said endoscope is inserted an in which said test object is disposed.

12. A video system according to claim 1, characterized by the fact that said image processing unit compensates brightness distribution, which diminishes radially toward an edge of the lens, of the overall endoscope image by means of image standardization conducted over all the image elements.

13. A video system according to claim 1, characterized by the fact that said image processing unit amplifies the signals from the individual image elements singly in such a manner that variances in the illumination of said object field are compensated.

14. A video system according to claim 12, characterized by the fact that said image processing unit corrects the overall endoscope image by electronic modification and/or resorting of single image elements in such a manner that transmission errors caused by faulty transmission properties of the fiber bundle can no longer be visually detected.

15. A video system according to claim 12 or 13, characterized by the fact that said image processing unit modifies the color information of said signals from image elements, which are applied by fibers having spectral transmission properties which deviate from that of the fiber bundle, by conversion in the color scale in such a manner that the color information of said image elements correspond to that of the adjacent image elements.

16. A video system according to claim 14, characterized by the fact that said image processing unit replaces said signals from the image elements, which are applied by defective fibers, with image information of adjacent image elements which are applied by non-defective fibers.

17. A video system according to claim 14, characterized by the fact that said image processing unit replaces signals from image elements, which are applied by spaces between the fibers, with the image information of adjacent image elements which are applied by light transmitting fibers.

18. A video system according to claim 14, characterized by the fact that the fiber bundle is an at least partly disordered bundle and that said image processing unit modifies the arrangement of individual image elements electronically in such a manner that the reproduced image corresponds to the image on the fiber bundle entry side.

19. A video system according to claim 14, characterized by the fact that said image processing unit amplifies said signals from the image elements, which are applied by fibers with relatively high transmission losses, in such a manner that the brightness of said image elements corresponds to the brightness of the adjacent image elements.

20. A video system according to claim 1, characterized by the fact that said image processing unit compensates color changes of the image caused by fluctuations in the color temperature of the lamp(s) of said illumination.

21. A video system according to claim 1, characterized by the fact that said image processing unit generates an electronic image field shutter which is smaller than an image field shutter of said endoscope.

22. A video system according to claim 1, characterized by the fact that said image processing unit subjects the image signal to manipulations selected from the group consisting off rotations, reflections, and combinations of these.

23. A process for calibrating an endoscopic video system comprising the steps of:
  disposing an endoscope before a test object,
  illuminating the test object with a source of light;
  imaging the test object on an image recorder having a plurality of imaging elements which generate a plurality of output signals;
  comparing each of the output signals which a desired output signal known for said test object to calculate and record a correction value specific for each imaging element and resulting due to one of a group of factor including: variances in the illumination, variances in sensitivity of said image recorder, and combinations of these, wherein the calculation of the correction value for each imaging element is independent of the calculation of the correction values for all other imaging elements;
  illuminating an object to be studied with the source of light to have a plurality of actual output signals generated by the imaging elements of the image recorder;
  adjusting each actual output signal generated by a respective individual image element with the respective recorded correction value.

24. A process according to claim 23, wherein said calculating step comprises calculating a correction matrix for a plurality of image element signals.

25. A process according to claim 23, wherein said disposing step comprises inserting an endoscope into a test cavity in such a manner that when recording the test chart there is a certain correspondence between an optical axis of the endoscope and a center of the test chart.

26. A process according to claim 23 including the step of repeating the other steps for calibrating the endoscope to a different test chart.

27. An endoscopic video system for correcting a video image of an object to be studied, comprising:

an optical system having opposite sides and including an endoscope at a one end of the optical system, a lens disposed in the endoscope, a light source and an illuminating fiber optic bundle between the source and the lens for illuminating an object field, the optical system projecting an image at its opposite side;

an electronic image recorder for recording the projected image at the opposite side of the optical system and having a multiplicity of image elements, each generating an output signal which represents intensity and color of an incident image spot projected on said image recorder; and an image processing unit connected to the image recorder and having a learning mode, wherein a known test object is introduced in the image field and imaged on the image recorder, and a correction value is generated from the output signal of each image element to compensate variances resulting due to one of a group of factors including: variances in the illumination, variances in sensitivity of said image recorder, and combination of these, the image processing unit recording the correction value for each image element, wherein the generation of the correction value for each image element is independent of the generation of the correction values for all other image elements, the image processing unit having a recording mode, wherein the object to be studied is introduced in the object field and imaged on the image recorder to have its video image enhanced by adjusting the output signal of each image element representing the object to be studied with the correction value recorded in the learning mode.

* * * * *